(12) United States Patent
Shima et al.

(10) Patent No.: US 10,898,448 B2
(45) Date of Patent: Jan. 26, 2021

(54) PATCH

(71) Applicant: HISAMITSU PHARMACEUTICAL CO., INC., Tosu (JP)

(72) Inventors: Takito Shima, Tsukuba (JP); Toshiyuki Matsudo, Tsukuba (JP); Kenji Ishigaki, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

(21) Appl. No.: 16/604,311

(22) PCT Filed: Apr. 19, 2018

(86) PCT No.: PCT/JP2018/016117
§ 371 (c)(1),
(2) Date: Oct. 10, 2019

(87) PCT Pub. No.: WO2018/198925
PCT Pub. Date: Nov. 1, 2018

(65) Prior Publication Data
US 2020/0054575 A1    Feb. 20, 2020

(30) Foreign Application Priority Data

Apr. 25, 2017  (JP) ................. 2017-086357
Jun. 30, 2017  (JP) ................. 2017-129601
Jun. 30, 2017  (JP) ................. 2017-129741

(51) Int. Cl.
*A61K 9/70*     (2006.01)
*A61K 31/485*   (2006.01)
*A61K 47/22*    (2006.01)
*A61K 47/32*    (2006.01)
*A61K 47/34*    (2017.01)

(52) U.S. Cl.
CPC .......... *A61K 9/7046* (2013.01); *A61K 31/485* (2013.01); *A61K 47/22* (2013.01); *A61K 47/32* (2013.01); *A61K 47/34* (2013.01)

(58) Field of Classification Search
CPC .. A61K 9/7061; A61K 9/7053; A61K 9/0014; A61K 9/7069; A61K 9/06; A61K 9/7084; A61K 9/7023; A61K 9/006; A61K 9/7076; A61K 9/127; A61K 9/0048; A61K 9/0056; A61K 9/0085; A61K 9/70; A61K 9/7092; A61K 9/7046; A61K 31/485; A61K 47/22; A61K 47/32; A61K 47/34
See application file for complete search history.

(56) References Cited

U.S. PATENT DOCUMENTS

| | | |
|---|---|---|
| 3,775,414 A | 11/1973 | Monkovic et al. |
| 4,626,539 A | 12/1986 | Aungst et al. |
| 2006/0078600 A1 | 4/2006 | Muller |
| 2008/0131490 A1 | 6/2008 | Hanatani et al. |
| 2008/0226697 A1 | 9/2008 | Yamaguchi et al. |
| 2009/0246265 A1 | 10/2009 | Stinchcomb et al. |
| 2012/0226245 A1* | 9/2012 | Kawamura .......... A61K 31/465 604/307 |
| 2014/0161865 A1 | 6/2014 | Higo et al. |
| 2015/0004215 A1 | 1/2015 | Yoshizaki et al. |
| 2017/0224630 A1 | 8/2017 | Noguchi et al. |

FOREIGN PATENT DOCUMENTS

| | | |
|---|---|---|
| EP | 2 740 472 A1 | 6/2014 |
| EP | 2 818 161 A1 | 12/2014 |
| JP | 61-083116 A | 4/1986 |
| JP | 2006-001859 A | 1/2006 |
| JP | 2006-045099 A | 2/2006 |
| JP | 2012-255043 A | 12/2012 |
| WO | 2005/102393 A1 | 11/2005 |
| WO | 2009/041714 A1 | 4/2009 |
| WO | 2016/060122 A1 | 4/2016 |
| WO | PCT/JP2018/016115 | 4/2018 |

OTHER PUBLICATIONS

Michal Svozil, et. al., "In Vitro Studies on Transdermal Permeation of Butorphanol", Drug Development and Industrial Pharmacy, 2007, pp. 559-567, vol. 33.
International Search Report for PCT/JP2018/016117 dated Jun. 26, 2018 [PCT/ISA/210].
International Preliminary Report on Patentability and Written Opinion for International Application No. PCT/JP2018/016117 dated Oct. 29, 2019.
U.S. Appl. No. 16/471,692, filed Jun. 20, 2019, Hisamitsu Pharmaceutical Co., Inc.
U.S. Appl. No. 16/605,268, filed Oct. 15, 2019, Hisamitsu Pharmaceutical Co., Inc.
Communication dated Apr. 22, 2020 from European Patent Office in EP Application No. 17889363.2.
Office Action dated Jun. 26, 2020 issued in U.S. Appl. No. 16/471,692.

* cited by examiner

*Primary Examiner* — Melissa L Fisher
*Assistant Examiner* — Ayaan A Alam
(74) *Attorney, Agent, or Firm* — Sughrue Mion, PLLC

(57) ABSTRACT

A patch comprises a backing layer and an adhesive layer, wherein the adhesive layer contains at least one selected from the group consisting of butorphanol and pharmaceutically acceptable salts thereof, and contains an adhesive base and an antioxidant containing a sulfur atom in its molecule.

2 Claims, No Drawings

PATCH

CROSS REFERENCE TO RELATED APPLICATIONS

This application is a National Stage of International Application No. PCT/JP2018/016117, filed on Apr. 19, 2018, which claims priority from Japanese Patent Application No. 2017-086357, filed on Apr. 25, 2017; Japanese Patent Application No. 2017-129601, filed on Jun. 30, 2017, and Japanese Patent Application No. 2017-129741, filed on Jun. 30, 2017.

TECHNICAL FIELD

The present invention relates to a patch, and more particularly relates to a patch containing butorphanol and/or a pharmaceutically acceptable salt thereof.

BACKGROUND ART

Butorphanol is a general name of 17-(cyclobutylmethyl) morphinan-3,14-diol having a molecular structure of morphinan skeleton. Butorphanol is a drug classified as an opioid analgesic and is generally used as an injectable formulation containing butorphanol tartrate which is a tartaric acid addition salt of butorphanol. Butorphanol is also disclosed as N-cyclobutylmethyl-3,14-dihydroxymorphinan, for example, in U.S. Pat. No. 3,775,414 (PLT 1).

Further, for example, M. Svozil et al., Drug Development and Industrial Pharmacy, 2007, 33(5), pp. 559-567 (NLT 1) teaches that butorphanol is used as a drug of a transdermal absorption preparation. Furthermore, International Publication No. WO2016/060122 (PLT 2) discloses a patch comprising a backing layer and an adhesive layer, the adhesive layer containing at least one selected from the group consisting of butorphanol and pharmaceutically acceptable salts thereof, and containing a higher aliphatic alcohol and an uncrosslinked polyvinylpyrrolidone containing no vinyl acetate as a constituent monomer. As an adhesive base contained in the adhesive layer of such a patch, there are known a rubber-based adhesive base, an acrylic adhesive base, a silicone-based adhesive base, a urethane-based adhesive base, and the like.

CITATION LIST

Patent Literature

[PTL 1] U.S. Pat. No. 3,775,414
[PTL 2] International Publication No. WO2016/060122

Non Patent Literature

[NPL 1] M. Svozil et al., Drug Development and Industrial Pharmacy, 2007, 33, pp. 559-567

SUMMARY OF INVENTION

Technical Problem

However, as a result of further studies, the present inventors have found that in a patch comprising a backing layer and an adhesive layer, the adhesive layer containing butorphanol and/or a pharmaceutically acceptable salt thereof and an adhesive base, the adhesive layer may contain a butorphanol oxidant as a degradation product of the butorphanol generated depending on a manufacturing method and a storage method. Pharmaceuticals are required to satisfy not only requirements concerning drug efficacy and formulation properties, but also various standards provided to ensure the safety. For such standards, for example, International Council for Harmonisation of Technical Requirements for Pharmaceuticals for Human Use (ICH) has provided "*Guidelines on impurities in pharmaceuticals among new active ingredient-containing drugs* (Original English title: IMPURITIES IN NEW DRUG PRODUCTS) (ICH Q3B (R2))". The butorphanol oxidant has a possibility of being regarded as a degradation product which is under an obligation to be reported in accordance with the above guideline. For this reason, a new demand to more surely prevent the aforementioned generation of the butorphanol oxidant has arisen on the pharmaceutical development.

The present invention has been made in view of the above demand, and has an object to provide a patch in which the generation of a butorphanol oxidant is remarkably inhibited as compared with a conventional patch.

Solution to Problem

The present inventors have continuously conducted earnest studies to achieve the above object, and consequently have found that a patch comprising a backing layer and an adhesive layer, the adhesive layer containing an adhesive base and at least one selected from the group consisting of butorphanol and pharmaceutically acceptable salts thereof (hereinafter referred to as "butorphanol and/or a pharmaceutically acceptable salt thereof" in some cases), generates almost no butorphanol oxidant and also can remarkably inhibit the generation of the butorphanol oxidant even for a long-term storage, when an antioxidant especially containing a sulfur atom in its molecule is further blended as an antioxidant to the adhesive layer. Moreover, the present inventors have also found that the adhesive layer (in particular, the adhesive layer containing a rubber-based adhesive base) in such a patch is also sufficiently inhibited from precipitating crystals (crystal precipitation of free forms of butorphanol), and have led to the completion of the present invention.

Specifically, a patch of the present invention is a patch comprising a backing layer and an adhesive layer, wherein the adhesive layer contains at least one selected from the group consisting of butorphanol and pharmaceutically acceptable salts thereof, and contains an adhesive base and an antioxidant containing a sulfur atom in its molecule.

In the patch of the present invention, the antioxidant containing a sulfur atom in its molecule is preferably 2-mercaptobenzimidazole.

Moreover, in the patch of the present invention, the content of the antioxidant containing a sulfur atom in its molecule is preferably 0.01 to 2.0% by mass relative to the total mass of the adhesive layer.

Further, in the patch of the present invention, the adhesive base is preferably at least one selected from the group consisting of rubber-based adhesive bases and silicone-based adhesive bases.

Furthermore, in the patch of the present invention, the content of the butorphanol and/or pharmaceutically acceptable salt thereof in the adhesive layer in terms of the mass of a tartaric acid addition salt of butorphanol is preferably 3 to 20% by mass relative to the total mass of the adhesive layer.

Still further, in the patch of the present invention, the adhesive layer preferably further contains at least one selected from the group consisting of tackifiers and plasticizers.

Advantageous Effects of Invention

According to the present invention, it is possible to provide a patch in which the generation of a butorphanol oxidant is remarkably inhibited as compared with the conventional patch. Further, according to the present invention, crystal precipitation in the adhesive layer is also sufficiently inhibited, which makes it possible to provide a patch excellent particularly in the stability over time.

DESCRIPTION OF EMBODIMENTS

Hereinafter, the present invention will be described in detail based on preferred embodiments thereof.

A patch of the present invention is a patch comprising a backing layer and an adhesive layer, wherein the adhesive layer contains at least one selected from the group consisting of butorphanol and pharmaceutically acceptable salts thereof, and contains an adhesive base and an antioxidant containing a sulfur atom in its molecule.

The patch of the present invention comprises the backing layer and the adhesive layer. The patch of the present invention preferably comprises the backing layer and the adhesive layer laminated on at least one of surfaces of the backing layer. As the backing layer, any layer publicly known as a backing layer for a patch may be used as appropriate without particular limitation as long as it can support the aforementioned adhesive layer. Examples of materials for the backing layer according to the present invention include: polyolefins such as polyethylene and polypropylene; an ethylene-vinyl acetate copolymer, a vinyl acetate-vinyl chloride copolymer, a polyvinyl chloride, and the like; polyamides such as nylon; polyesters such as polyethylene terephthalate (PET), polybutylene terephthalate, and polyethylene naphthalate; cellulose derivatives; synthetic resins such as polyurethane; and metals such as aluminum. Among them, the polyester and polyethylene terephthalate are preferable from the viewpoints of non-drug-adsorbing property and drug impermeability. Examples of the forms of the backing layer include: films; sheets such as sheets, porous sheets, and foamed sheets; cloths such as woven fabrics, knitted fabrics, and nonwoven fabrics; foils; and laminates thereof. Then, the thickness of the backing layer is not particular limited but is preferably within a range of 5 to 1000 μm from the viewpoints of easiness of work for applying a patch and manufacturability.

The patch of the present invention may further include a release liner on a surface of the adhesive layer opposite from the backing layer. As such a release liner, there are films, sheets, or laminates thereof which are made of materials including: polyolefins such as polyethylene and polypropylene; an ethylene-vinyl acetate copolymer, a vinyl acetate-vinyl chloride copolymer, a polyvinyl chloride, and the like; polyamides such as nylon; polyesters such as polyethylene terephthalate; cellulose derivatives; synthetic resins such as polyurethane; aluminum; paper; and so on. Preferably, in each of these release liners, the surface to be in contact with the adhesive layer is release-treated by a silicone-containing compound coating, a fluorine-containing compound coating, or the like so that the release liner can be easily peeled off from the adhesive layer.

<Drug>

The adhesive layer according to the present invention contains, as a drug, at least one selected from the group consisting of butorphanol and pharmaceutically acceptable salts thereof. In the present invention, butorphanol is defined as 17-(cyclobutylmethyl)morphinan-3,14-diol, which is expressed by a molecular formula of $C_{21}H_{29}NO_2$.

In the present invention, the form of butorphanol contained in the adhesive layer may be a free form, a pharmaceutically acceptable salt thereof, or a free form obtained by desalting a pharmaceutically acceptable salt of butorphanol during manufacturing and/or in the formulation manufactured, or may be one of them or a mixture of two or more of them. The pharmaceutically acceptable salt of butorphanol is preferably an acid addition salt from the viewpoint that the stability of the drug tends to further improve. Examples of the acid in the acid addition salt include hydrochloric acid, sulfuric acid, nitric acid, phosphoric acid, phosphorous acid, hydrobromic acid, maleic acid, malic acid, ascorbic acid, tartaric acid, lauric acid, stearic acid, palmitic acid, oleic acid, myristic acid, lauryl sulfuric acid, linolenic acid, and fumaric acid. Among them, a tartaric acid addition salt (butorphanol tartrate) expressed by the following structural formula (1) is preferred as the pharmaceutically acceptable salt of butorphanol.

[Chem. 1]

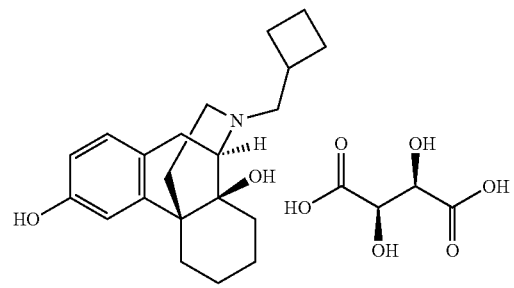

(1)

In the present invention, the content of butorphanol and/or a pharmaceutically acceptable salt thereof contained in the adhesive layer (the content of the butorphanol, the content of the pharmaceutically acceptable salt of butorphanol, or the total content of the butorphanol and the salt if both of them are contained. The same applies below) in terms of the tartaric acid addition salt of butorphanol is preferably 3 to 20% by mass, more preferably 3 to 15% by mass, even more preferably 3 to 12% by mass relative to the total mass of the adhesive layer. If the content of the butorphanol and/or the pharmaceutically acceptable salt thereof is less than the aforementioned lower limit, the skin permeability of butorphanol tends to decrease. On the other hand, if the content exceeds the aforementioned upper limit, crystals of butorphanol tend to easily precipitate and the adhesive force of the adhesive layer tends to decrease.

In the present invention, when the content of the butorphanol and/or the pharmaceutically acceptable salt thereof contained in the adhesive layer is specified as the content in terms of the tartaric acid addition salt of butorphanol per unit area of the adhesive layer, the content is preferably 0.2 to 2.0 mg/cm$^2$, more preferably 0.2 to 1.5 mg/cm$^2$, and even more preferably 0.2 to 1.2 mg/cm$^2$. If the content of the butorphanol and/or the pharmaceutically acceptable salt thereof per unit area is less than the aforementioned lower limit, the maximum transdermal flux rate of butorphanol tends to be small. On the other hand, if the content exceeds the aforementioned upper limit, crystals of butorphanol tend to easily precipitate and the adhesive force of the adhesive layer tends to decrease.

The adhesive layer according to the present invention may further contain a drug other than the butorphanol and pharmaceutically acceptable salts thereof as long as the drug does not impair the effect of the present invention. Examples of the other drug include nonsteroidal antiinflammatory analgesics (such as diclofenac, indomethacin, ketoprofen, felbinac, loxoprofen, ibuprofen, flurbiprofen, tiaprofen, acemetacin, sulindac, etodolac, tolmetin, piroxicam, meloxicam, ampiroxicam, naproxen, azapropazone, methyl salicylate, glycol salicylate, valdecoxib, celecoxib, rofecoxib, and amfenac), antipyretic analgesics (such as acetaminophen), antihistamines (such as diphenhydramine, chlorpheniramine, mequitazine, and homochlorocyclodine), antihypertensive agents (such as diltiazem, nicardipine, nilvadipine, metoprolol, bisoprolol, and trandolapril), antiparkinsonian drugs (such as pergolide, ropinirole, bromocriptine, and selegiline), bronchodilators (such as tulobuterol, isopretenolol, and salbutamol), antiallergic agents (such as ketotifen, loratadine, azelastine, terfenadine, cetirizine, and acitazanorast), local anesthetics (such as lidocaine and dibucaine), neuropathic pain remedies (such as pregabalin), non-narcotic analgesics (such as buprenorphine, tramadol, and pentazocine), anesthetic analgesics (such as morphine, oxycodone, and fentanyl), drugs for organa urinaria (such as oxybutynin and tamsulosin), drugs for psychoneurosis (such as promazine and chlorpromazine), steroid hormone agents (such as estradiol, progesterone, norethisterone, cortisone, and hydrocortisone), antidepressants (such as sertraline, fluoxetine, paroxetine, and citalopram), anti-dementia drugs (such as donepezil, rivastigmine, and galantamine), antipsychotic drugs (such as risperidone and olanzapine), central nerve stimulants (such as methylphenidate), drugs for osteoporosis treatment (such as raloxifene and alendronate), prophylactic drugs for breast cancer (such as tamoxifen), anti-obesity drugs (such as mazindole and dibutramine), insomnia remedies (such as melatonin), and anti-rheumatic drugs (such as actarit). One of these drugs may be used alone, or two or more of them may be used in combination. When the other drugs are contained in the adhesive layer, the total content of the other drugs is preferably 50% by mass or less relative to the total mass of the adhesive layer.

<Adhesive Base>

The adhesive layer according to the present invention contains an adhesive base. As the adhesive base, a rubber-based adhesive base, a silicone-based adhesive base, and an acrylic adhesive base are usable. Among them, the adhesive base is preferably at least one selected from the group consisting of rubber-based adhesive bases and silicone-based adhesive bases, is more preferably a rubber-based adhesive base or a combination of a rubber-based adhesive base and a silicone-based adhesive base from the viewpoint that the patch tends to be capable of exhibiting the effect of inhibiting crystal precipitation in particular, and is even more preferably a combination of a rubber-based adhesive base and a silicone-based adhesive base from the viewpoints that the patch can have superior skin permeability of butorphanol, and exhibit a high level of adhesion to the skin (the adhesion of a patch in the present invention is defined as a property in which the surface of the patch in contact with the skin firmly sticks to the skin and does not peel off).

As the rubber-based adhesive base, there are natural rubbers and synthetic rubbers. From the viewpoint that the adhesive layer for a patch more tends to maintain a sufficient adhesive force, the rubber-based adhesive base is more preferably at least one selected from the group consisting of synthetic rubbers not having a polar functional group (such as a hydroxyl group, a carboxyl group, and an amino group), such as a styrene-isoprene-styrene block copolymer (SIS), an isoprene rubber, polyisobutylene (PIB), a styrene-butadiene-styrene block copolymer (SBS), a styrene-butadiene rubber (SBR), and polybutene. One of these rubber-based adhesive bases may be used alone, or two or more of them may be used in combination. However, from the viewpoint that the adhesive layer for a patch more tends to maintain a sufficient adhesive force, it is particularly preferable to use any one of SIS and PIB alone, or to use a combination of SIS and PIB at a mass ratio (the mass of SIS:the mass of PIB) in a range of 9:1 to 1:9 (even more preferably in a range of 9:1 to 1:3).

In the present invention, the silicone-based adhesive base refers to a polymer (polysiloxane) containing siloxane units each expressed by the following structural formula (2) and having siloxane bonds (—Si—O—) as a main chain.

[Chem. 2]

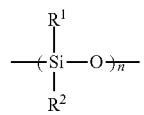

(2)

In the siloxane unit expressed by the formula (2), n represents a numerical value of 2 or more. Then, $R^1$ and $R^2$ each independently represent a group bonded to a Si atom. $R^1$ and $R^2$ are not particularly limited, but it is preferable that each of $R^1$ and $R^2$ be independently a hydrogen atom, a hydroxyl group, an alkyl group, an alkenyl group, an aryl group, or an alkoxy group. The polymer may be any of a linear polymer, a branched polymer, and a cyclic polymer, or may be a composite of them. The ends of the polymer are not particularly limited, but it is preferable that each ends be independently a hydrogen atom, a hydroxyl group, an alkyl group, an alkenyl group, an aryl group, an alkoxy group, a trimethylsilyl group, or a trimethylsilyloxy group.

Agents usable as the silicone-based adhesive base according to the present invention include silicone rubbers referred to as MQ (polydimethylsiloxane, $R^1$ and $R^2$ in the formula (2) are methyl groups), VMQ (polymethylvinylsiloxane), PMQ (polymethylphenylsiloxane), and PVMQ (polyphenylvinylmethyl siloxane) according to the ASTM standard (ASTM D 1418); mixtures each containing at least one of the aforementioned rubbers and a silicone resin, such as polyditrimethylsilyl siloxane, other than the silicone rubber; and the like. One of them may be used alone, or two or more of them may be used in combination. When a silicone resin other than the silicone rubber is mixed, the content of the silicone resin is preferably 0.1 to 20% by mass relative to the total mass of the silicone-based adhesive base. The silicone-based adhesive base according to the present invention preferably contains at least one silicone rubber selected from the group consisting of polydimethylsiloxane, polymethylvinylsiloxane, polymethylphenylsiloxane, and polyphenylvinylmethyl siloxane. Moreover, in the silicone-based adhesive base according to the present invention, it is more preferable that the silanol groups contained in the silicone rubber be each independently capped (end-capped) with an alkyl group, an alkenyl group, an aryl group, an alkoxy group, a trimethylsilyl group, or a trimethylsilyloxy group.

In addition, commercially available agents may be used as these silicone-based adhesive bases. Examples of them are silicone adhesives provided by Dow Corning Corp. under the following product numbers: BIO-PSA7-410X, BIO-PSA7-420X, BIO-PSA7-430X, BIO-PSA7-440X, BIO-PSA7-450X, BIO-PSA7-460X (X in the preceding numbers is independently 1 or 2), BIO-PSA AC7-4201, BIO-PSA AC7-4301, BIO-PSA AC7-4302, MD7-4502, MD7-4602, 7-9700, MG7-9800, MG7-9850, BIO-PSA 7-4560 (a hot-melt silicone adhesive agent), and the like. One of them may be used alone or two or more of them may be used in combination.

Moreover, for the purpose of enhancing the cohesiveness of the adhesive layer, the silicone-based adhesive base may be modified as follows. For example, in the case where the agent has methyl groups, a peroxide is further blended for dehydrogenation, thereby crosslinking the methyl groups by removing hydrogen atoms from the methyl groups. In the case where the agent has vinyl groups, the vinyl groups are crosslinked by bonding a crosslinking agent composed of a siloxane compound containing SiH groups. In the case where the agent has hydroxyl groups (in other words, has silanol groups), the silanol groups are crosslinked by dehydrative condensation.

As the acrylic adhesive base, there are acrylic adhesive bases, listed as adhesive agents in "Pharmaceutical Excipients Directory 2016 (Japanese Version) (edited by International Pharmaceutical Excipients Council Japan)", such as a copolymer of acrylic acid/octyl acrylate, a copolymer of 2-ethylhexyl acrylate/vinyl pyrrolidine, a copolymer of acrylic ester/vinyl acetate, a copolymer of 2-ethylhexyl acrylate/2-ethylhexyl methacrylate/dodecyl methacrylate, a copolymer resin of methyl acrylate/2-ethylhexyl acrylate, a copolymer of 2-ethylhexyl acrylate/methyl acrylate/acrylic acid/glycidyl methacrylate, a copolymer of 2-ethylhexyl acrylate/vinyl acetate/hydroxyethyl acrylate/glycidyl methacrylate, a copolymer of 2-ethylhexyl acrylate/diacetone acrylamide/acetoacetoxyethyl methacrylate/methyl methacrylate, a copolymer of ethyl acrylate/methyl methacrylate, an acrylic polymer contained in an acrylic resin alkanolamine solution, and additionally a copolymer of 2-ethylhexyl acrylate/vinyl acetate/butyl acrylate/acrylic acid, a copolymer of acrylic acid/2-ethylhexyl acrylate/vinyl acetate, a copolymer of acrylic acid/butyl acrylate/2-ethylhexyl acrylate, a copolymer of acrylic acid/methyl acrylate/2-ethylhexyl acrylate, a copolymer of acrylic acid/2-ethylhexyl acrylate/2-hydroxyethyl acrylate/methyl methacrylate/butyl acrylate, a copolymer of 4-hydroxybutyl (meth)acrylate, a copolymer of 2-ethylhexyl acrylate/vinyl acetate, a copolymer of 2-ethylhexyl acrylate/methyl methacrylate/butyl acrylate, a copolymer of 2-ethylhexyl acrylate/methacrylic acid, and the like. One of them may be used alone or two or more of them may be used in combination.

In the present invention, the content of the adhesive base contained in the adhesive layer (in the case of a combination of two or more adhesive bases, the total content of them) is preferably 15 to 96% by mass and more preferably 20 to 90% by mass relative to the total mass of the adhesive layer. If the content of the adhesive base is less than the aforementioned lower limit, the adhesive force of the adhesive layer tends to decrease. On the other hand, if the content exceeds the aforementioned upper limit, the skin permeability of butorphanol tends to decrease.

Moreover, in the present invention, when the rubber-based adhesive base is contained as the adhesive base in the adhesive layer, the content thereof is preferably 5 to 95% by mass, more preferably 15 to 95% by mass, and even more preferably 20 to 95% by mass relative to the total mass of the adhesive layer. If the content of the rubber-based adhesive base is less than the aforementioned lower limit, the adhesive force of the adhesive layer tends to decrease. On the other hand, if the content exceeds the aforementioned upper limit, the skin permeability of butorphanol tends to decrease.

Additionally, if the rubber-based adhesive base and the silicone-based adhesive base are contained as the adhesive base, the content of the rubber-based adhesive base is preferably 5 to 95% by mass, more preferably 5 to 85% by mass, even more preferably 5 to 50% by mass, and particularly preferably 7 to 40% by mass relative to the total mass of the adhesive layer. If the content of the rubber-based adhesive base is less than the aforementioned lower limit, the effect of improving the adhesion of the adhesive layer to the skin tends not to be produced sufficiently, and it tends to be difficult to uniformly mix the rubber-based adhesive base and the silicone-based adhesive base during manufacturing. On the other hand, if the content exceeds the aforementioned upper limit, the content of the silicone-based adhesive base decreases relative to the content of the rubber-based adhesive base. In this case, the effect of improving the adhesion of the adhesive layer to the skin, in particular, the adhesion under the warm water conditions or the high humidity conditions tends not to be produced sufficiently.

Further, in the present invention, if the silicone-based adhesive base is contained as the adhesive base in the adhesive layer, the content thereof is preferably 1 to 95% by mass, more preferably 5 to 95%, and even more preferably 5 to 85% by mass relative to the total mass of the adhesive layer. If the content of the silicone-based adhesive base is less than the aforementioned lower limit, the adhesive force of the adhesive layer tends to decrease. On the other hand, if the content exceeds the aforementioned upper limit, the skin permeability of butorphanol tends to decrease.

Still further, if the rubber-based adhesive base and the silicone-based adhesive base are contained as the adhesive base, the content of the silicone-based adhesive base is preferably 1 to 47% by mass, more preferably 1 to 45% by mass, even more preferably 1 to 42% by mass, much more preferably 1 to 38% by mass, and particularly preferably 1 to 36% by mass relative to the total mass of the adhesive layer. If the content of the silicone-based adhesive base is less than the aforementioned lower limit, the effect of improving the adhesion of the adhesive layer to the skin, in particular, the adhesion under the warm water conditions or the high humidity conditions tends not to be produced sufficiently. On the other hand, if the content exceeds the aforementioned upper limit, the content of the rubber-based adhesive base decreases relative to the content of the silicone-based adhesive base. In this case, the adhesive force of the adhesive layer tends to decrease, and it tends to be difficult to uniformly mix the rubber-based adhesive base and the silicone-based adhesive base during manufacturing.

Furthermore, in the present invention, if the rubber-based adhesive base and the silicone-based adhesive base are contained as the adhesive base in the adhesive layer, the mass ratio of the rubber-based adhesive base to the silicone-based adhesive base (the mass of the rubber-based adhesive base:the mass of the silicone-based adhesive base) is preferably 9.5:0.5 to 1.9:8.1, more preferably 9.5:0.5 to 2.5:7.5, even more preferably 9.5:0.5 to 3.0:7.0, and particularly preferably 9.5:0.5 to 4.0:6.0. In addition, the mass ratio is also preferably 9.0:1.0 to 1.9:8.1, more preferably 8.0:2.0 to 1.9:8.1, even more preferably 7.6:2.4 to 1.9:8.1, and particularly preferably 5.0:5.0 to 2.5:7.5. if the content of the silicone-based adhesive base relative to the rubber-based adhesive base is less than the aforementioned lower limit, the effect of improving the adhesion of the adhesive layer to the skin, in particular, the adhesion under the warm water conditions or the high humidity conditions tends not to be produced sufficiently. On the other hand, if the content exceeds the aforementioned upper limit, the effect of improving the adhesion of the adhesive layer to the skin tends not to be produced sufficiently, and it tends to be difficult to uniformly mix the rubber-based adhesive base and the silicone-based adhesive base during manufacturing.

<Antioxidant>

The adhesive layer according to the present invention contains an antioxidant containing a sulfur atom in its molecule as an antioxidant. Additionally containing the antioxidant containing a sulfur atom in its molecule, the adhesive layer can remarkably inhibit generation of a butorphanol oxidant without decreasing the basic properties of a drug such as skin permeability.

As an antioxidant containing a sulfur atom in its molecule according to the present invention, preferable examples include imidazole-based antioxidants (such as 2-mercaptobenzimidazole (2-MBI)), sodium pyrosulfite, sodium thioglycolate, N-acetylcysteine, and thioglycerol. One of them may be used alone or two or more of them may be used in combination. Among them, from the viewpoint that the effect of inhibiting generation of a butorphanol oxidant tends to be particularly high, the antioxidant containing a sulfur atom in its molecule according to the present invention is more preferably at least one selected from the imidazole-based antioxidants, and is particularly preferably 2-mercaptobenzimidazole.

In the present invention, the content of the antioxidant containing a sulfur atom in its molecule contained in the adhesive layer (in the case of a combination of two or more kinds, the total content of them. The same applies below) is preferably 0.01 to 2.0% by mass, more preferably 0.01 to 1.0% by mass, even more preferably 0.04 to 1.0% by mass, further preferably 0.05 to 1.0% by mass, particularly preferably 0.1 to 1.0% by mass, and further particularly preferably 0.1 to 0.5% by mass relative to the total mass of the adhesive layer. If the content of the antioxidant containing a sulfur atom in its molecule is less than the aforementioned lower limit, the effect of inhibiting generation of a butorphanol oxidant tends to decrease. On the other hand, even if the adhesive layer contains the antioxidant in the amount exceeding the aforementioned upper limit, the adhesive layer tends to have no expectation that the effect of inhibiting generation of a butorphanol oxidant can be further enhanced.

The adhesive layer according to the present invention may further contain an antioxidant other than the antioxidant containing a sulfur atom in its molecule as long as the antioxidant does not impair the effect of the present invention. Examples of the other antioxidant include: phenolic antioxidants such as dibutylhydroxytoluene (BHT) and butylhydroxyanisole (BHA); tocopherol and ester derivatives thereof; organic acids such as ascorbic acid and citric acid; fatty acid esters such as ascorbyl palmitate esters and ascorbyl stearate esters; paraben-based compounds such as methyl paraben and ethyl paraben; organic acid salts such as sodium citrate, sodium EDTA, and EDTA. One of them may be used alone or two or more of them may be used in combination. If such other antioxidants are further contained in the adhesive layer, the content in total is 5.0% by mass or less relative to the total mass of the adhesive layer.

<Absorption Enhancer>

The adhesive layer according to the present invention may further contain an absorption enhancer (transdermal absorption enhancer) as long as the absorption enhancer does not impair the effect of the present invention. An example of the absorption enhancer is at least one selected from the group consisting of aliphatic alcohols, fatty acid esters, fatty acid amides, and aliphatic alcohol ethers. Among them, preferred is at least one selected from the group consisting of aliphatic alcohols and fatty acid esters from the viewpoint that the maximum transdermal flux rate of butorphanol (Jmax) tends to be particularly high.

(Aliphatic Alcohol)

The aliphatic alcohol according to the present invention is preferably a monovalent aliphatic alcohol having 6 to 20 carbon atoms. If the number of carbon atoms in the aliphatic alcohol is less than the aforementioned lower limit, the skin irritation tends to be strong. On the other hand, if the number exceeds the aforementioned upper limit, a waxy agglomerate may be formed in the formulation. Examples of the aliphatic alcohols having 6 to 20 carbon atoms include lauryl alcohol, myristyl alcohol, cetyl alcohol, stearyl alcohol, isostearyl alcohol, oleyl alcohol, linolenyl alcohol, octyldodecanol, and mixtures thereof. Among them, a particularly preferable one is one selected from the group consisting of isostearyl alcohol, oleyl alcohol, and octyldodecanol from the viewpoint that the skin permeability of butorphanol tends to further improve.

(Fatty Acid Ester)

The fatty acid ester according to the present invention is preferably one selected from the group consisting of alkyl esters of fatty acids having 6 to 20 carbon atoms (fatty acid alkyl esters), esters of fatty acids having 6 to 20 carbon atoms with glycerol or polyglycerol (glycerol fatty acid esters), esters of fatty acids having 6 to 20 carbon atoms with polyoxyalkylene (polyoxyalkylene fatty acid esters), and esters of fatty acids having 6 to 20 carbon atoms with saccharides (fatty acid esters of saccharides).

In the present invention, the fatty acid alkyl ester is an ester compound of a fatty acid having 6 to 20 carbon atoms with a lower alkyl alcohol. Examples of such fatty acid alkyl esters include isopropyl myristate, oleyl oleate, isopropyl palmitate, triethyl citrate, ethyl linoleate, hexyl laurate, cetyl myristate, octyl dodecyl myristate, decyl oleate, otyldodecyl oleate, octyldodecyl neodecanoate, cetyl ethylhexanoate, cetyl palmitate, stearyl stearate, and mixtures of them. Among them, preferred is at least one selected from the group consisting of isopropyl myristate and isopropyl palmitate from the viewpoint that the skin permeability of butorphanol tends to further improve.

In the present invention, examples of the glycerol fatty acid esters include glycerol monolaurate (monolaurin), polyglycerol monolaurate, glycerol monostearate (monostearin), polyglycerol monostearate, glycerol monooleate (monoolein), polyglycerol monooleate, glyceryl trimyristate, glyceryl tri(caprylic-capric acid), glyceryl triisostearate, and glyceryl trioctanoate. It is preferable that the polymerization degree in the polyglycerol be 50 or less. Among them, a preferable glycerol fatty acid ester is at least one selected from the group consisting of glycerol monolaurate, polyglycerol monolaurate, glycerol monostearate, polyglycerol monostearate, glycerol monooleate, and polyglycerol monooleate.

Further, the glycerol fatty acid ester may be one in which a polyoxyethylene (POE) group is further added to an OH group in the glycerol. The degree of oxyethylene polymerization in the polyoxyethylene group is preferably 50 or less.

In the present invention, the polyoxyalkylene fatty acid ester is a compound in which a polyoxyalkylene such as ethylene glycol, polyethylene glycol, propylene glycol, polypropylene glycol, or a copolymer compound of oxyethylene and oxypropylene is ester-bonded to a portion of a carboxy group in a fatty acid having 6 to 20 carbon atoms. Such fatty acid esters with polyoxyalkylene include ethylene glycol monolaurate, polyoxyethylene monolaurate (hereinafter, polyoxyethylene is abbreviated to "POE" and oxyethylene is abbreviated to "OE" in some cases), propylene glycol monolaurate (PGML), polyoxypropylene monolaurate (hereinafter, polyoxypropylene is abbreviated to "POP" and oxypropylene is abbreviated to "OP" in some cases), ethylene glycol monopalmitate, POE monopalmitate, propylene glycol monopalmitate, POP monopalmitate, ethylene glycol monostearate, POE monostearate, propylene glycol monostearate, POP monostearate, ethylene glycol monooleate, POE monooleate, propylene glycol monooleate, POP monooleate, dioleate propylene glycol, and polyethylene glycol distearate. It is preferable that the degree of polymerization in each of the copolymers with POE, POP, OE, and OP be independently 50 or less. Among them, a particularly preferable polyoxyalkylene fatty acid ester is propylene glycol monolaurate from the viewpoint that the maximum transdermal flux rate of butorphanol (Jmax) tends to be particularly high.

In the present invention, the fatty acid ester of saccharide is a compound in which a saccharide is ester-bonded to a portion of a carboxy group of a fatty acid having 6 to 20 carbon atoms. As the saccharides, there are tetrasaccharides (erythrose and threose), penta-saccharides (xylose and arabinose), hexa-saccharides (glucose and galactose), sugar alcohols (xylitol and sorbitol), disaccharides (sucrose, lactose, and maltose), and the like. Fatty acid esters with such saccharides include sorbitan monolaurate (Span 20), sorbitan monopalmitate (Span 40), sorbitan monostearate (Span 60), sorbitan tristearate (Span 65), sorbitan monooleate (Span 80), sorbitan trioleate, and sorbitan sesquioleate (Span 83).

In addition, the fatty acid ester with the saccharide may be one in which a polyoxyethylene (POE) group is further added to an OH group in a sugar residue. The degree of oxyethylene polymerization in the polyoxyethylene group is preferably 50 or less. Such compounds are polysorbate 20 (Tween 20), polysorbate 40 (Tween 40), polysorbate 60 (Tween 60), polysorbate 65 (Tween 65), polysorbate 80 (Tween 80), and the like.

(Fatty Acid Amide)

The fatty acid amide according to the present invention is an amide of a fatty acid having 6 to 20 carbon atoms. Examples thereof include lauric acid diethanolamide, oleic acid diethanolamide, stearic acid diethanolamide, ethylene bis-stearic acid amide, stearic acid monoamide, oleic acid monoamide, ethylene bis-oleic acid amide, erucic acid monoamide, and mixtures of them.

(Aliphatic Alcohol Ether)

In the present invention, the aliphatic alcohol ether is a compound in which polyoxyalkylene such as ethylene glycol, polyethylene glycol, propylene glycol, polypropylene glycol, a copolymer compound of oxyethylene and oxypropylene, glycerol, or polyglycerol is ether-bonded to a portion of an OH group in an aliphatic alcohol having 6 to 20 carbon atoms. Examples of such aliphatic alcohol ethers include POE oleyl ether, POE lauryl ether, POE cetyl ether, POE stearyl ether, POE octyl dodecyl ether, POE palmityl ether, and mixtures of them.

Other examples of the absorption enhancers which may be contained in the adhesive layer according to the present invention include POE hydrogenated castor oils, lecithins, phospholipids, soybean oil derivatives, triacetins, and so on.

Moreover, in the adhesive layer according to the present invention, it is also preferable that the absorption enhancer be a surface-activating compound that functions as a surfactant. Among the above-listed compounds, a preferable surface-activating compound is, for example, at least one selected from the group consisting of propylene glycol monolaurate, sorbitan monooleate, glycerol monolaurate, glycerol monooleate, polysorbate 20, polysorbate 40, polysorbate 60, and polysorbate 80. Moreover, the surface-activating compound is preferably non-ionic.

In the present invention, in the case where such an absorption enhancer is further contained in the adhesive layer, the preferable content (in the case of a combination of two or more enhancers, the total content of them) is such that the mass ratio of the butorphanol and/or pharmaceutically acceptable salt thereof to the absorption enhancer (the mass of butorphanol and/or a pharmaceutically acceptable salt thereof in terms of a tartaric acid addition salt:the mass of the absorption enhancer) is preferably 20:1 to 1:10, and more preferably 15:1 to 1:7. In this case, the content of the absorption enhancer relative to the total mass of the adhesive layer is preferably 1 to 30% by mass and more preferably 1 to 20% by mass. If the content of the absorption enhancer is within the aforementioned range, the transdermal flux rate of butorphanol tends to be further enhanced.

<Additive>

The adhesive layer according to the present invention may further contain additives such as adsorbents, desalting agents, tackifiers, plasticizers, solubilizing agents for drugs, fillers, stabilizers, preservatives, and so on as long as the additives do not impair the effect of the present invention.

(Adsorbent)

As the adsorbents, there are inorganic and/or organic substances having hygroscopicity. More specifically, there are mineral substances such as talc, kaolin, and bentonite; silicon compounds such as fumed silica (such as Aerosil (registered trademark)) and hydrated silica; metallic compounds such as zinc oxide and dried aluminum hydroxide gel; weak acids such as lactic acid and acetic acid; sugars such as dextrin; and high molecular weight polymers such as polyvinylpyrrolidone, aminoalkyl methacrylate copolymer, crospovidone, carboxyvinyl polymer, and butyl methacrylate methyl methacrylate copolymer. One of them may be used alone, or two or more of them may be used in combination. Among them, the adhesive layer according to the present invention preferably further contains polyvinylpyrrolidone (PVP) from the viewpoint that precipitation of crystals of the butorphanol can be more inhibited.

In the case where an adsorbent (preferably polyvinylpyrrolidone) is further contained in the adhesive layer, the content of the adsorbent is preferably 0.05 to 2 mg/cm$^2$ in terms of the content per unit area of the adhesive layer or is 1 to 20% by mass in terms of the content relative to the total mass of the adhesive layer.

Further, the mass ratio of the butorphanol and/or pharmaceutically acceptable salt thereof to the polyvinylpyrrolidone (the mass of the butorphanol and/or a pharmaceutically acceptable salt thereof in terms of the tartaric acid addition salt:the mass of the polyvinylpyrrolidone) is preferably 20:1 to 1:10. If the content of the polyvinylpyrrolidone is less than the aforementioned lower limit, it tends to be unlikely to produce a further effect of inhibiting precipitation of crystals of the butorphanol. On the other hand, if the content exceeds the aforementioned upper limit, the skin permeability of butorphanol tends to decrease and the adhesive force of the adhesive layer tends to decrease.

(Desalting Agent)

The desalting agent is blended mainly for the purpose of converting all or part of a basic drug into a free form. Such a desalting agent is not particularly limited. For example, in the case of preparing a formulation containing butorphanol in free form by blending an acid addition salt of butorphanol as the drug, the desalting agent is preferably a basic substance, and more preferably a metal ion-containing desalting agent or a basic nitrogen atom-containing desalting agent. As the metal ion-containing desalting agent, there are sodium acetate (including anhydrous sodium acetate), sodium hydroxide, potassium hydroxide, magnesium hydroxide, sodium hydrogencarbonate, potassium hydrogencarbonate, sodium citrate, sodium lactate, and the like. One of them may be used alone, or two or more of them may be used in combination. Among them, sodium acetate and sodium hydroxide are particularly preferable as the desalting agent. Here, the adhesive layer according to the present invention may further contain a compound derived from the basic drug and the desalting agent (for example, in the case where butorphanol tartrate and sodium acetate are mixed together, the adhesive layer may further contain sodium tartrate). In the case where the desalting agent and the compound derived from the basic drug and the desalting agent are further contained in the adhesive layer, the content in terms of the desalting agent is preferably 0.5 to 5 acid-base equivalents and more preferably 0.5 to 4 acid-base equivalents with respect to 1 acid-base equivalent of the butorphanol in terms of the tartaric acid addition salt from the viewpoint that the degradation of the drug is inhibited.

(Tackifier)

The tackifier is blended mainly for the purpose of enhancing the tackiness of the adhesive base, preferably the rubber-based adhesive base. As such tackifiers, there are, for example, tackifier resins such as rosin-based resins, terpene-based resins, petroleum-based resins, phenol-based resins, and xylene-based resins. One of them may be used alone, or two or more of them may be used in combination. In the case where such a tackifier is further contained in the adhesive layer, the content thereof (in the case of a combination of two or more tackifiers, the total content of them) is preferably 0.5 to 60% by mass, more preferably 0.5 to 50% by mass, even more preferably 3 to 50% by mass, and particularly preferably 3 to 40% relative to the total mass of the adhesive layer from the viewpoints of improvement in the adhesive force of the adhesive layer and/or relaxation of local irritation at peeling-off.

(Plasticizer)

The plasticizer is blended mainly for the purpose of adjusting properties such as the adhesive property of the adhesive layer, the flowability of the adhesive layer during manufacturing, and the transdermal absorbability of the drug. Examples of such a plasticizer include silicone oil; petroleum-based oils such as paraffin-based process oils, naphthene-based process oils, and aromatic process oils; squalane and squalene; plant oils such as olive oil, *camellia* oil, castor oil, tall oil, and peanut oil; dibasic acid esters such as dibutyl phthalate and dioctyl phthalate; liquid rubbers such as polybutene and liquid isoprene rubber; diethylene glycol, polyethylene glycol, propylene glycol, and dipropylene glycol; and the like. One of them may be used alone, or two or more of them may be used in combination. Among them, the silicone oil, the liquid paraffin, and the liquid polybutene are preferable as the plasticizer. In the case where such a plasticizer is further contained in the adhesive layer, the content thereof (in the case of a combination of two or more plasticizers, the total content of them) is preferably 0.1 to 60% by mass, more preferably 0.5 to 25% by mass and 3 to 50% by mass, and even more preferably 3 to 20% by mass relative to the total mass of the adhesive layer from the viewpoints of improvement in the adhesive force of the adhesive layer and/or relaxation of local irritation at peeling-off.

(Solubilizing Agent)

The solubilizing agent is blended mainly for the purpose of promoting dissolution of the drug. Examples of such a solubilizing agent include organic acids such as acetic acid, aliphatic alcohols, and surfactants. One of them may be used alone, or two or more of them may be used in combination. Among them, the organic acids and the aliphatic alcohols are preferable as the solubilizing agent.

(Filler)

The filler is blended mainly for the purpose of adjusting the adhesive force of the adhesive layer. Example of such a filler include aluminum hydroxide, calcium carbonate, magnesium carbonate; silicates such as aluminum silicate and magnesium silicate; silicic acid, barium sulfate, calcium sulfate, calcium zincate, zinc oxide, and titanium oxide. One of them may be used alone or two or more of them may be used in combination.

In the case where the aforementioned additives are further contained in the adhesive layer, the content in total is preferably 70% by mass or less relative to the total mass of the adhesive layer.

The total mass of the adhesive layer according to the present invention per unit area (the area of an attachment surface) is preferably 25 to 250 $g/m^2$ and more preferably 40 to 200 $g/m^2$. If the mass per unit area is less than the aforementioned lower limit, there are tendencies to decrease the skin permeability of butorphanol, decrease the adhesive force of the adhesive layer, and make it difficult to control the thickness of the adhesive layer during manufacturing. On the other hand, if the mass per unit area exceeds the aforementioned upper limit, there are tendencies to excessively increase the skin permeability of butorphanol for a patch intended to be attached for a long term, and make it difficult to control the thickness of the adhesive layer during manufacturing.

Moreover, the area of the attachment surface of the adhesive layer according to the present invention may be adjusted as appropriate depending on a treatment purpose or an application target, and is usually within a range of 0.5 to 200 $cm^2$.

The patch of the present invention may be a packaged formulation in which the patch is enclosed (preferably hermetically sealed) in a package during a period after manufacturing until use. The package is not particularly limited, but any of those usually used as packages for patches may be used as appropriate. For example, plastic (for example, polyethylene) packaging bags, plastic packaging bags in each of which a metal layer (for example, an aluminum layer) is formed, metal packaging bags (for example, an aluminum packaging bag), and the like are preferably used.

The packaged formulation in which the patch is enclosed in the package may further include deoxidizing means. As the deoxidizing means, there are: an oxygen absorbers using iron powder or an oxygen absorber containing vitamin C as a main component, which is enclosed in the package (more specifically, such as ageless series (manufactured by Mitsubishi Gas Chemical Company, Inc.) and PharmaKeep series (manufactured by Mitsubishi Gas Chemical Company, Inc.)); and the package including a layer having a deoxidizing function (more specifically a layer mixed with powder of aluminum, zinc, manganese, copper, iron, hydrosulfite, activated carbon, or the like).

The patch of the present invention may be manufactured by using any publicly-known patch manufacturing method as appropriate without any particular limitation. For example, first, butorphanol and/or a pharmaceutically acceptable salt thereof, the adhesive base, and the antioxidant containing a sulfur atom in its molecule together with an absorption enhancer, a solvent, the additives, and so on as needed are kneaded according to a generally known method to obtain a uniform adhesive layer composition. As the solvent, absolute ethanol, toluene, heptane, methanol, or the like may be used. Subsequently, this adhesive layer composition is applied onto the surface of the backing layer (usually the surface on one side) so as to have a desired mass per unit area, followed drying and removing the solvent, if necessary, by heating, thereby forming the adhesive layer. Further, the resultant backing/adhesive layer is cut into pieces in a desired shape as needed to obtain the patch of the present invention.

The method for manufacturing the patch of the present invention may further comprise a step of sticking the release liner onto the surface of the adhesive layer opposite from the backing layer. In this case, the method may comprise: first applying the adhesive layer composition in a desired mass per unit area to the surface of one side of the release liner to form the adhesive layer; thereafter sticking the backing layer onto the surface of the adhesive layer opposite from the release liner; and cutting them into pieces in a desired shape as needed to obtain the patch of the present invention. Then, the obtained patch may be hermetically sealed as needed in the package, thereby forming a packaged formulation.

EXAMPLES

Hereinafter, the present invention will be described more specifically based on Examples and Comparative Examples; however, the present invention is not limited to the following Examples. Here, Examples and Comparative Examples were examined in an oxidant amount measurement test, a crystal precipitation evaluation test, and a skin permeation test in the following methods.

<Oxidant Amount Measurement Test>

At least one group of patches selected from patches immediately after production, patches after storage in a state hermetically sealed in polyethylene packaging bags at 60° C. for 1 week, and patches after storage in a state hermetically sealed in polyethylene packaging bags at 40° C. and 75% RH for 3 months (the area of the attachment surface of the adhesive layer: 2.5 cm$^2$) was measured in terms of the amount of an oxidant in the adhesive layer. To measure the amount of the oxidant, firstly, the release liner was removed from each patch, the patch was placed in a glass centrifuge tube, and 0.5 mL of tetrahydrofuran was added to the centrifuge tube, followed by shaking to dissolve the adhesive layer. Then, 5 mL of a liquid mixture of acetonitrile and water (acetonitrile:water=1:1 (volume ratio)) was further added to the resultant solution, followed by shaking. After that, part of the solution was collected and filtered through a membrane filter. Subsequently, the obtained filtrate was used as a sample solution, the areas of the peak areas of the butorphanol and/or a salt thereof and the butorphanol oxidant in the sample solution were determined by high performance liquid chromatography. The high performance liquid chromatography was conducted by using a detector: an ultraviolet absorption photometer (a measurement wavelength: 280 nm) and a column: ODS column, while controlling a concentration gradient such that a mixing ratio of a mobile phase A (12.6 mM ammonium bicarbonate buffer solution (pH9.0)) and a mobile phase B (methanol) (mobile phase A/mobile phase B (volume ratio)) was changed from 55/45 to 35/65 during a time period after the sample injection: 0 to 38.5 minutes. Then, the amount of the oxidant in the adhesive layer of each patch [% by mass] was calculated in accordance with the following formula:

The amount of oxidant [% by mass]=$A_T/A_S \times 100$

[in the formula, $A_T$ denotes the area of the peak area of the butorphanol oxidant, and $A_S$ denotes the area of the peak area of the butorphanol and/or salt thereof]. As for the peak area of the butorphanol oxidant, the peak area appearing at a position with a relative retention time (RRT) of around 0.24 with respect to the retention time of the butorphanol was measured as the peak area of the butorphanol oxidant.

<Crystal Precipitation Evaluation Test>

At least one group of patches selected from patches immediately after production, patches after storage in an unpackaged state at 40° C. and 75% RH for 1 day, patches after storage in an unpackaged state at 40° C. and 75% RH for 10 days, and patches after storage in an unpackaged state at 40° C. and 75% RH for 1 month (the area of the attachment surface of the adhesive layer: 2.5 cm$^2$) was evaluated in terms of crystal precipitation in the adhesive layer. Three patches were evaluated by visually observing the surfaces of the adhesive layers, and crystal precipitation in the adhesive layer of each of the patches was evaluated according to the following criteria:

A: No crystal precipitation was observed;

B: The patch was usable as a formulation but crystal precipitation was partly observed; and C: Crystal precipitation was observed on the entire surface and the patch was inadequate as a formulation.

<Skin Permeation Test (In Vitro Hair-Less Mouse Skin Permeation Test)>

First, the skin of the hairless mouse body was peeled off and the fat was removed from the skin. The patch was cut in a size of 2.5 cm$^2$ and was applied to the epidermis side of the skin after the release liner was removed from the patch. This was set in a flow-through Franz cell for permeation test with the dermis side being in contact with a receptor solution, and the cell was filled with the receptor solution (PBS). Subsequently, the receptor solution was delivered at a flow rate of about 2.5 ml/hr while circulating warmed circulation water around the outer periphery so that the receptor solution was kept at 32° C., and the receptor solution was collected every fourth hour for up to 24 hours. The concentration of butorphanol in the collected receptor solution (in terms of tartaric acid) was measured by high performance liquid chromatography and an hourly amount of butorphanol permeated through the skin per unit area of the adhesive layer (in terms of tartaric acid, unit: μg/cm$^2$/hr) was calculated for each of the collection times, and the maximum value among the obtained values was regarded as the maximum transdermal flux rate (Jmax).

Example 1

First, 6.0 parts by mass of butorphanol tartrate, 22.6 parts by mass of a silicone-based adhesive base (silicone adhesive agent, product number: BIO-PSA7-4201, manufactured by Dow Corning Corp.), 19.1 parts by mass of a rubber-based adhesive base (SIS:PIB=4:6 (mass ratio)), a 22.0 parts by mass of a tackifier (tackifier resin), 11.7 parts by mass of a plasticizer (liquid paraffin), 0.5 parts by mass of 2-mercaptobenzimidazole (2-MBI), and 18.1 parts by mass of other ingredients (a desalting agent, an absorption enhancer, and an adsorbent) were added to an appropriate amount of a solvent (absolute ethanol and toluene), followed by mixing to obtain an adhesive layer composition. Then, the obtained adhesive layer composition was applied onto a release liner (a film made of polyethylene terephthalate and processed by release treatment), and the solvent was removed by drying, thereby forming the adhesive layer having a mass per unit area of 80 g/m². A backing layer (a film made of polyethylene terephthalate) was laminated onto the surface of the obtained adhesive layer opposite from the release liner, and thereby a patch was obtained in which the backing layer/the adhesive layer/the release liner were laminated in this order.

Comparative Examples 1 to 6

Patches were obtained in the same way as in Example 1 except that various kinds of antioxidants (Comparative Example 1: dibutylhydroxytoluene, Comparative Example 2: dibutylhydroxyanisole, Comparative Example 3: ascorbic acid, Comparative Example 4: propyl gallate, Comparative Example 5: tocopherol acetate, and Comparative Example 6: EDTA and disodium) were blended in place of the 2-mercaptobenzimidazole (2-MBI) and the ingredients presented below in Table 1 were used as the ingredients blended in the adhesive layer composition.

Comparative Example 7

A patch was obtained in the same way as in Example 1 except that the ingredients presented below in Table 1 were used as the ingredients blended in the adhesive layer composition without blending the 2-mercaptobenzimidazole (2-MBI).

Comparative Example 8

A patch was obtained in the same way as in Comparative Example 7 except that the rubber-based adhesive base, the tackifier, and the plasticizer were not blended, and the ingredients presented below in Table 1 were used as the ingredients blended in the adhesive layer composition.

Comparative Example 9

A patch was obtained in the same way as in Comparative Example 7 except that an acrylic adhesive base (product name: MAS811, manufactured by CosMED Pharmaceutical Co. Ltd.) was blended in place of the silicone-based adhesive base, the rubber-based adhesive base, the tackifier, and the plasticizer, and the ingredients presented below in Table 1 were used as the ingredients blended in the adhesive layer composition.

Examples 2 to 10

Each patch was obtained in the same way as in Example 1 except that the ingredients presented below in Table 2 were used as the ingredients blended in the adhesive layer composition.

The patches obtained in Examples 1 to 10 and Comparative Examples 1 to 9 were examined in the above-specified oxidant amount measurement test, crystal precipitation evaluation test, and skin permeation test. Table 1 presents the blended ingredients (excluding a solvent) of the adhesive layer composition of the patch obtained in each of Example 1 and Comparative Examples 1 to 9 and the oxidant amounts immediately after production, after storage at 60° C. for 1 week, and after storage at 40° C. (75% RH) for 3 months, and Table 2 presents the blended ingredients (excluding a solvent) of the adhesive layer composition of the patch obtained in each of Examples 1 to 10 and Comparative Example 7 and the oxidant amounts immediately after production and after storage at 60° C. for 1 week. In addition, Table 3 presents the results of the crystal precipitation evaluation test conducted on the patches obtained in Examples 3, 4, 6, and 7 and Comparative Example 7. Here, in each of Examples 3, 4, 6, and 7 and Comparative Example 7, three patches examined in the crystal precipitation evaluation test had no difference in the surface state of the adhesive layer, and demonstrated an evaluation result presented in Table 3.

TABLE 1

|  | Ex. 1 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|---|---|---|
| Adhesive layer composition [parts by mass] | | | | | | | | | | |
| Butorphanol tartrate | 6.0 | 6.0 | 6.0 | 6.0 | 6.0 | 6.0 | 6.0 | 6.0 | 5.0 | 9.0 |
| Silicone-based adhesive base | 22.6 | 22.6 | 22.6 | 22.6 | 22.6 | 22.6 | 22.6 | 22.8 | 74.3 | — |
| Rubber-based adhesive base | 19.1 | 19.1 | 19.1 | 19.1 | 19.1 | 19.1 | 19.1 | 19.2 | — | — |
| Tackifier | 22.0 | 22.0 | 22.0 | 22.0 | 22.0 | 22.0 | 22.0 | 22.1 | — | — |
| Plasticizer | 11.7 | 11.7 | 11.7 | 11.7 | 11.7 | 11.7 | 11.7 | 11.8 | — | — |
| Acrylic adhesive base | — | — | — | — | — | — | — | — | — | 68.9 |
| 2-MBI | 0.5 | — | — | — | — | — | — | — | — | — |
| Dibutylhydroxytoluene | — | 0.5 | — | — | — | — | — | — | — | — |
| Dibutylhydroxyanisole | — | — | 0.5 | — | — | — | — | — | — | — |
| Ascorbic acid | — | — | — | 0.5 | — | — | — | — | — | — |
| Propyl gallate | — | — | — | — | 0.5 | — | — | — | — | — |
| Tocopherol acetate | — | — | — | — | — | 0.5 | — | — | — | — |
| EDTA - disodium | — | — | — | — | — | — | 0.5 | — | — | — |
| Others | 18.1 | 18.1 | 18.1 | 18.1 | 18.1 | 18.1 | 18.1 | 18.1 | 20.7 | 22.1 |
| Total | 100 | 100 | 100 | 100 | 100 | 100 | 100 | 100 | 100 | 100 |
| Oxidant amount [% by mass] | | | | | | | | | | |
| Immediately after production | 0 | 0.21 | 0.25 | 0.96 | 0.18 | 0.24 | 0.23 | 0.25 | — | — |

TABLE 1-continued

| | Ex. 1 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|---|---|---|
| 60° C. after 1 week | 0.04 | 2.36 | 2.57 | 3.18 | 2.80 | 2.59 | 2.72 | 2.72 | — | — |
| 40° C. after 3 months | — | — | — | — | — | — | — | — | 2.80 | 2.07 |

TABLE 2

| | Ex. 2 | Ex. 3 | Ex. 4 | Ex. 5 | Ex. 6 | Ex. 7 | Ex. 1 | Ex. 8 | Ex. 9 | Ex. 10 | Comp. Ex. 7 |
|---|---|---|---|---|---|---|---|---|---|---|---|
| Adhesive layer composition [parts by mass] | | | | | | | | | | | |
| Butorphanol tartrate | 6.0 | 6.0 | 6.0 | 6.0 | 6.0 | 6.0 | 6.0 | 6.0 | 6.0 | 6.0 | 6.0 |
| Silicone-based adhesive base | 22.6 | 22.6 | 22.6 | 22.6 | 22.6 | 22.6 | 22.6 | 22.6 | 7.6 | 7.5 | 22.8 |
| Rubber-based adhesive base | 19.1 | 19.1 | 19.1 | 19.1 | 19.1 | 19.1 | 19.1 | 19.1 | 24.7 | 24.3 | 19.2 |
| Tackifier | 22.0 | 22.0 | 22.0 | 22.0 | 22.0 | 22.0 | 22.0 | 22.0 | 28.4 | 28.1 | 22.1 |
| Plasticizer | 12.19 | 12.17 | 12.15 | 12.10 | 12.05 | 12.00 | 11.70 | 11.20 | 15.20 | 15.00 | 11.80 |
| 2-MBI | 0.01 | 0.03 | 0.05 | 0.1 | 0.15 | 0.2 | 0.5 | 1.0 | 0.05 | 1.0 | — |
| Others | 18.1 | 18.1 | 18.1 | 18.1 | 18.1 | 18.1 | 18.1 | 18.1 | 18.1 | 18.1 | 18.1 |
| Total | 100 | 100 | 100 | 100 | 100 | 100 | 100 | 100 | 100 | 100 | 100 |
| Oxidant amount [%] | | | | | | | | | | | |
| Immediately after production | — | 0.21 | 0.14 | — | 0.08 | 0.06 | 0 | 0 | 0 | 0 | 0.25 |
| 60° C. after 1 week | 1.89 | 1.86 | 0.83 | 0.53 | 0.07 | — | 0.04 | 0 | 0.36 | 0 | 2.72 |

TABLE 3

| | Ex. 3 | Ex. 4 | Ex. 6 | Ex. 7 | Comp. Ex. 7 |
|---|---|---|---|---|---|
| Immediately after production | A | A | A | A | A |
| 40° C. after 1 day | A | A | A | A | B |
| 40° C. after 1 month | — | A | A | A | B |

From the results presented in Tables 1 and 2, it was apparently found that the patches of the present invention (Examples 1 to 10) in which the antioxidant containing a sulfur atom in its molecule, specifically, 2-mercaptobenzimidazole (2-MBI) was blended as the antioxidant produced almost no butorphanol oxidant or no butorphanol oxidant at all even after a long-term storage, and therefore were capable of remarkably inhibiting the generation of the butorphanol oxidant. Moreover, as is apparent from the results presented in Table 3, the patches of the present invention were also observed particularly inhibiting crystal precipitation in the adhesive layer. Here, as a result of the above-specified skin permeation test, it was found that all the patches obtained in Examples 1 to 10 exhibited sufficient skin permeability and did not cause a decrease in the skin permeability of the drug.

Moreover, as is apparent from the results presented in Table 1, the patches in which even the other antioxidants conventionally used as the antioxidants for patches were blended (Comparative Examples 1 to 6) generated the butorphanol oxidant immediately after production, as in the case of the patch (Comparative Example 7) in which no antioxidant was blended. It should be noted that, in Comparative Example 1, patches in which the content of the dibutylhydroxytoluene was increased to two times (1.0 parts by mass) were also produced and examined in the oxidant amount measurement test in the same way, with the result that the effect of inhibiting the generation of the butorphanol oxidant was not observed even though the content was increased.

Comparative Examples 10 to 13

The patch obtained in Comparative Example 7 was cut into patches in a size of 2.5 cm$^2$, and the obtained patches were each hermetically sealed in a polyethylene packaging bag together with an oxygen absorber (Comparative Example 10: Ageless ZJ-15PT (manufactured by Mitsubishi Gas Chemical Company, Inc.), Comparative Example 11: PharmaKeep KC (manufactured by Mitsubishi Gas Chemical Company, Inc.), and Comparative Example 12: PharmaKeep KD (manufactured by Mitsubishi Gas Chemical Company, Inc.)) or without any oxygen absorber (Comparative Example 13), thereby obtaining a packaged formulation.

The packaged formulations obtained in Comparative Examples 10 to 13 were stored at 60° C. for 5 days, and thereafter the oxidant amount in the adhesive layer in each of the patches in the packaged formulations was measured in the method described in the above-specified oxidant amount measurement test. Table 4 presents the blended ingredients (excluding a solvent) of the adhesive layer composition of the packaged formulation obtained in each of Comparative Examples 10 to 13, the oxygen absorber, and the oxidant amount after storage at 60° C. for 5 days.

TABLE 4

|  | Comp. Ex. 10 | Comp. Ex. 11 | Comp. Ex. 12 | Comp. Ex. 13 |
|---|---|---|---|---|
| Adhesive layer composition [parts by mass] | | | | |
| Butorphanol tartrate | 6.0 | 6.0 | 6.0 | 6.0 |
| Silicone-based adhesive base | 22.8 | 22.8 | 22.8 | 22.8 |
| Rubber-based adhesive base | 19.2 | 19.2 | 19.2 | 19.2 |
| Tackifier | 22.1 | 22.1 | 22.1 | 22.1 |
| Plasticizer | 11.8 | 11.8 | 11.8 | 11.8 |
| 2-MBI | — | — | — | — |
| Others | 18.1 | 18.1 | 18.1 | 18.1 |
| Total | 100 | 100 | 100 | 100 |
| Deoxidizing means | Ageless ZJ-15PT | PharmaKeep KC | PharmaKeep KD | — |
| Oxidant amount [%] | | | | |
| 60° C. after 5 days | 2.60 | 2.11 | 2.08 | 2.84 |

The patches of the present invention in which the antioxidant containing a sulfur atom in its molecule was blended produced the remarkable effect of inhibiting generation of the butorphanol oxidant, as compared with the cases presented in Table 4 where only the oxygen absorbers were used as the deoxidizing means in (Comparative Examples 10 to 12) and where no oxygen absorber was used (Comparative Example 13).

Examples 11 and 12 and Comparative Examples 14 and 15

Each patch was obtained in the same way as in Example 1 except that the ingredients presented below in Table 5 were used as the ingredients blended in the adhesive layer composition.

The patches obtained in Examples 11 and 12 and Comparative Examples 14 and 15 were examined in the above-specified oxidant amount measurement test and crystal precipitation evaluation test. Table 5 presents the blended ingredients (excluding a solvent) of the adhesive layer composition of the patch obtained in each of Examples 11 and 12 and Comparative Examples 14 and 15, the oxygen absorber, and the oxidant amounts immediately after production and after storage at 60° C. for 1 week. Table 6 presents the evaluation results of the crystal precipitation evaluation test conducted on the patches obtained in Examples 11 and 12 and Comparative Examples 14 and 15. Here, in each of Examples 11 and 12 and Comparative Examples 14 and 15, three patches examined in the crystal precipitation evaluation test had no difference in the surface state of the adhesive layer, and demonstrated an evaluation result presented in Table 6.

TABLE 5

|  | Ex. 11 | Comp. Ex. 14 | Ex. 12 | Comp. Ex. 15 |
|---|---|---|---|---|
| Adhesive layer composition [parts by mass] | | | | |
| Butorphanol tartrate | 15.0 | 12.0 | 4.0 | 4.0 |
| Silicone-based adhesive base | 6.1 | 6.5 | 75.45 | 75.6 |
| Rubber-based adhesive base | 19.7 | 21.1 | — | — |
| Tackifier | 22.8 | 24.3 | — | — |
| Plasticizer | 12.05 | 13.00 | — | — |
| 2-MBI | 0.15 | — | 0.15 | — |
| Others | 24.2 | 23.1 | 20.4 | 20.4 |
| Total | 100 | 100 | 100 | 100 |
| Oxidant amount [%] | | | | |
| Immediately after production | 0.03 | 0.62 | 0 | 0.16 |
| 60° c. after 1 week | 0.03 | 2.34 | 0 | 1.96 |

TABLE 6

|  | Ex. 11 | Comp. Ex. 14 | Ex. 12 | Comp. Ex. 15 |
|---|---|---|---|---|
| Immediately after production | A | A | A | A |
| 40° C. after 1 day | A | B | A | A |
| 40° C. after 10 days | A | B | A | A |

From the results presented in Table 5, it was apparently found that, even in the case where the content of the butorphanol and/or pharmaceutically acceptable salt thereof was high (Example 11) and the case where the adhesive layer contained no rubber-based adhesive base (Example 12), the patches of the present invention in which the antioxidant containing a sulfur atom in its molecule, specifically, the 2-mercaptobenzimidazole (2-MBI) was blended as the antioxidant produced almost no butorphanol oxidant or no butorphanol oxidant at all after a long-term storage and therefore were capable of remarkably inhibiting the generation of the butorphanol oxidant.

INDUSTRIAL APPLICABILITY

According to the present invention, it is possible to provide a patch in which the generation of a butorphanol oxidant is remarkably inhibited as compared with a conventional patch as described above. Moreover, according to the present invention, crystal precipitation in the adhesive layer is also sufficiently inhibited, so that patches excellent particularly in the stability over time can be provided.

The invention claimed is:

1. A patch comprising a backing layer and an adhesive layer, wherein
    the adhesive layer contains, butorphanol tartrate, an adhesive base and an antioxidant containing a sulfur atom in its molecule, and wherein
    the antioxidant containing a sulfur atom in its molecule is 0.05 to 1.0% by mass relative to the total mass of the adhesive layer,
    the butorphanol tartrate is 3 to 20% by mass relative to the total mass of the adhesive layer,
    the antioxidant containing a sulfur atom in its molecule is 2-mercaptobenzimidazole, and the adhesive base is at least one selected from the group consisting of rubber-based adhesive bases and silicone-based adhesive bases.

2. The patch according to claim 1, wherein the adhesive layer further contains at least one selected from the group consisting of tackifiers and plasticizers.

\* \* \* \* \*